United States Patent [19]

Stevens

[11] Patent Number: 5,078,722
[45] Date of Patent: Jan. 7, 1992

[54] METHOD AND APPARATUS FOR REMOVING DEPOSITS FROM A VESSEL

[75] Inventor: Robert C. Stevens, Williston, Fla.

[73] Assignee: Cordis Corporation, Miami Lakes, Fla.

[21] Appl. No.: 567,316

[22] Filed: Aug. 14, 1990

[51] Int. Cl.⁵ .............................................. A61B 17/32
[52] U.S. Cl. .................................... 606/159; 604/22
[58] Field of Search ............... 128/751, 754, 755; 604/22; 606/159, 167, 168, 170, 180

[56] References Cited

U.S. PATENT DOCUMENTS

| | | | |
|---|---|---|---|
| 4,669,469 | 6/1987 | Gifford, III et al. | |
| 4,857,046 | 8/1989 | Stevens et al. | |
| 4,917,085 | 4/1990 | Smith. | |
| 4,923,462 | 5/1990 | Stevens | 606/159 |
| 4,979,939 | 12/1990 | Shiber | 606/159 |

Primary Examiner—Stephen C. Pellegrino
Assistant Examiner—Steven J. Shumaker
Attorney, Agent, or Firm—Watts, Hoffmann, Fisher & Heinke Co.

[57] ABSTRACT

A catheter for insertion into a subject and for use in removing deposits from inner wall linings of a vessel, typically a blood vessel. The catheter includes a cutting member located at its distal end which is used to separate deposits from the inner wall linings of the vessel that have been forced into a cavity at the catheter's distal end. As deposits are separated from the vessel, the cavity can become filled with such deposits and a pumping device can be inserted into the catheter and rotated with respect to the catheter to withdraw the deposits. Further treatment can cause the pumping member to also become filled with the deposits. In the event this occurs, the pumping device is retracted from the catheter, cleaned and reinserted for further treatment.

11 Claims, 2 Drawing Sheets

METHOD AND APPARATUS FOR REMOVING DEPOSITS FROM A VESSEL

FIELD OF THE INVENTION

The present invention concerns a catheter for removing deposits from the inner wall linings of a vessel, such as a blood vessel.

BACKGROUND ART

U.S. Pat. No. 4,669,469 to Gifford III et al.

a device for removing material from a blood vessel. A catheter is disclosed having a distally located cutter that separates deposits from the blood vessel. The catheter also defines a passageway which extends along its length to accommodate a flexible drive cable for rotating the cutter. An inflatable balloon at the distal end of the catheter is inflated to force the catheter wall against an atheroma attached to an inner lining of the vessel. This forces the atheromas into a cavity so it can be separated from the vessel wall by the cutter.

One perceived problem with the structure disclosed in the '469 patent is periodic clogging of the catheter with use. In the event the cavity becomes filled with material dislodged from the inner wall lining of the vessel, the entire catheter must be withdrawn from the subject. The cavity is then cleaned so that the catheter can be reinserted for further treatment of the vessel.

DISCLOSURE OF THE INVENTION

The present invention concerns a device for removing unwanted deposits from the interior of a vessel, such as a blood vessel. In accordance with one embodiment of the present invention, a mechanism is provided for removing the deposits once they are separated from the inner wall linings of the vessel. This preferred embodiment uses a core member which can be inserted into an elongated catheter and pushed distally into a catheter cavity and then rotated to withdraw deposits from the cavity into the catheter body. In the event the core member becomes clogged with deposits, it can be retracted from inside the catheter, cleaned and reinserted.

One use of the apparatus of the invention is with a catheter having an elongated body and a distally located cutting member for separating deposits from inner wall linings of a vessel. The catheter defines a cavity at its distal end that receives deposits separated from the vessel inner wall lining. The core member can be inserted into the catheter body and routed to the vicinity of the cavity. The core member includes a surface for withdrawing the deposits into the catheter body away from the distally located cavity as the elongated member and the catheter body are relatively rotated.

In accordance with a preferred design, the catheter includes a distally located balloon that is inflated to bring the catheter into contact with the deposits to be removed. These deposits enter the distal cavity through an opening in a side wall of the cavity so that they can be separated from the inner wall lining of the vessel by the cutting member.

In accordance with the preferred design, the cutting member is rotated by a tubular transmission that defines a passageway extending from the proximal to distal end of the catheter. The elongated core member defines a pumping surface that spirals about the member. The core member is inserted into the catheter through the passageway in the transmission and routed to the vicinity of the catheter cavity. The elongated member is then rotated with respect to the catheter and the pumping surface withdraws accumulated deposits from within the catheter cavity.

In the event the region between the spiralling surface of the elongated member and the inner surface of the transmission becomes clogged with deposits, the elongated member is pulled from the catheter and cleaned to remove the deposits. This cleaning process can be conducted while leaving the catheter within the subject. The ability to remove the deposits from the catheter without removing the catheter from the subject is one important object and advantage of the present invention. This and other objects, advantages and features of the invention will become better understood from a detailed description of the invention which is described in conjunction with the accompanying drawings.

BEST MODE FOR CARRYING OUT THE INVENTION

Figure 1:
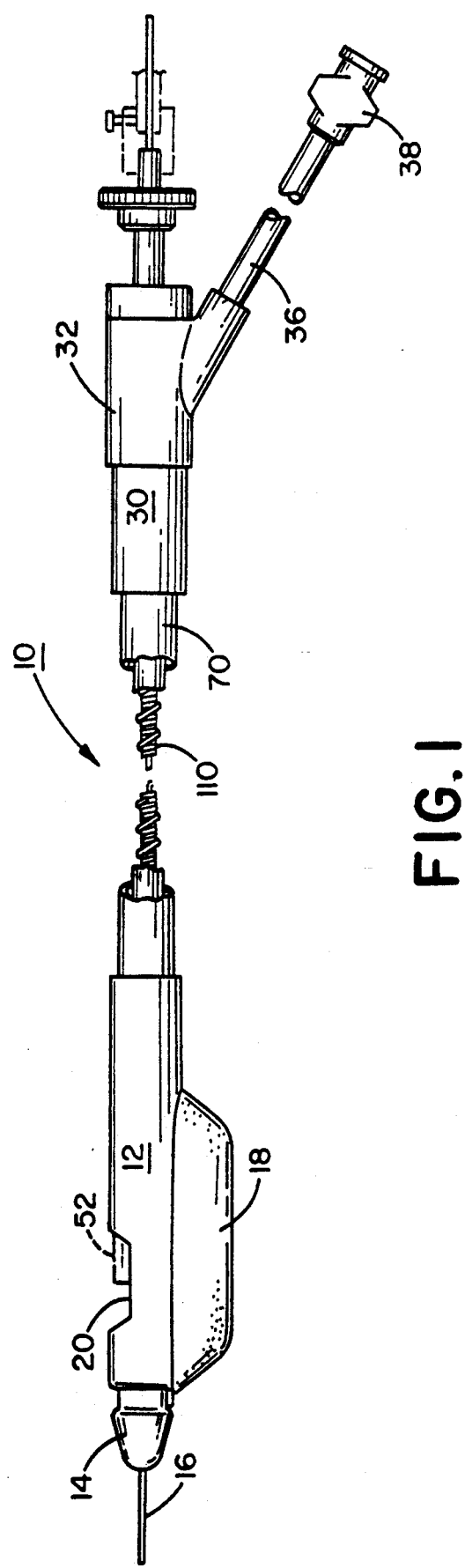
FIG. 1 is a schematic depiction of an elongated catheter designed for removing deposits from the inner wall linings of a vessel, typically a blood vessel.

Turning now to the drawings, FIG. 1 depicts a catheter 10 having a proximal end which remains outside the subject during treatment of the subject and a distal end which is routed into a subject to a region of the vessel having deposits which are to be removed. In the preferred embodiment of the present invention, the catheter 10 is specifically designed for treatment of blood vessels so that the catheter is long enough to be inserted into the subject and routed through the subject's cardiovascular system to a diseased or obstructed region within a subject blood vessel.

A catheter distal end 12 has a tapered tip 14 which can be pushed into the subject's cardiovascular system and guided with the aid of an elongated flexible guidewire 16. Techniques for inserting a catheter such as the one depicted in FIG. 1 are known in the prior art. The catheter's distal end also includes an inflatable balloon 18. When inflated, the balloon 18 engages an inner wall lining of the vessel which is being treated. The engagement between the balloon 18 and the vessel (not shown) causes a portion of the catheter wall opposite the balloon to be pushed into engagement with the inner wall lining of the vessel.

During insertion of the catheter 10, an attending physician monitors progress of the catheter on a viewing screen. The physician injects a radio-opaque dye through the catheter 10 and the dye exits the catheter's distal tip 14. This facilitates monitoring the movement of the distal end 12 as the physician manipulates the catheter from outside the subject. In particular, the physician can monitor the relationship of a distal opening 20 with respect to a deposit such as an atheroma attached to an inner wall lining of the blood vessel.

At the catheter's proximal end 30 a bifurcating adaptor 32 defines in-line and branch passageways into the catheter 10. A side branch passageway 34 (FIG. 2) defines an infusion port that routes fluid for inflating the balloon into the catheter. A flexible tube 36 having a leur fitting 38 at one end engages the adapter 32 for routing fluid into the catheter 10. Once the catheter 10 is properly oriented within the vessel, the balloon 18 is inflated and deposits adhering to the inner walls of the vessel are forced through the opening 20 into a cavity 50 (FIG. 2) defined by the catheter's distal end 12.

Figure 2:
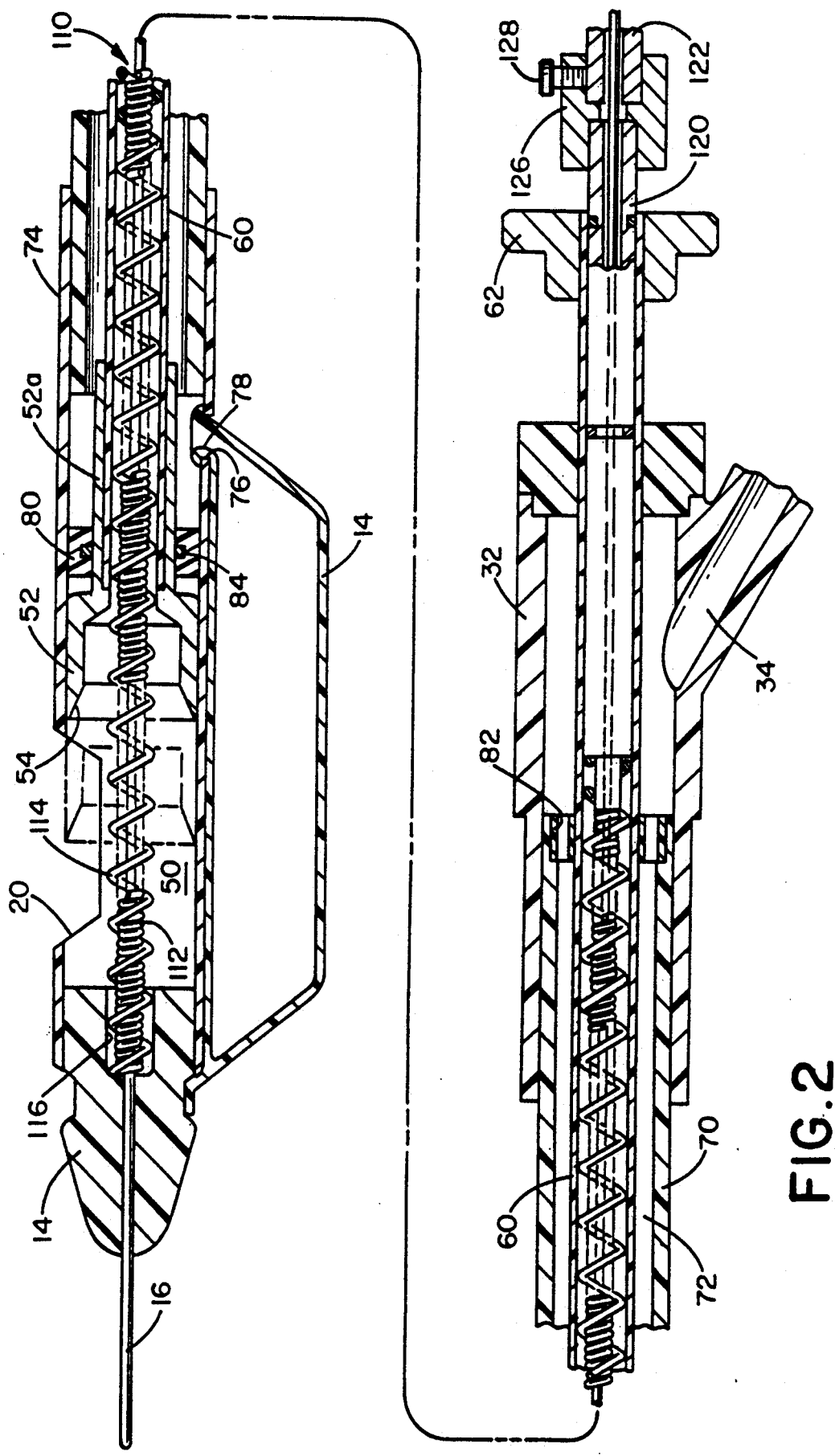
FIG. 2 is an enlarged, partially sectioned view of both a proximal end and a distal end of the catheter depicted in FIG. 1.

As seen most clearly in FIG. 2, the distally located cavity 50 is generally cylindrical in shape and is bounded at one end by the catheter's distal tip 14. An opposite end of the cavity 50 is bounded by a moveable cutting member 52 that can be moved axially back and forth through the cavity 50 as well as rotated. When the cutting member 52 is pushed distally toward the tip 14, a circular cutting edge 54 engages undesirable deposits or material forced into the cavity 50 as the balloon 18 inflates.

Manipulation of the cutting member 52 and more specifically coordinated back and forth movement and rotation of the cutting member 52 is controlled by the attending physician from outside the subject. A flexible, hollow drive shaft 60 extends the length of the catheter and connects the cutting member 52 to a manually manipulatable knob 62.

At the catheter's distal end, the cutting member 52 defines a metal collar 52a that fits over a distal end of the flexible drive shaft 60. A radially inner surface of the collar 52a is machined to a depth approximately equal to the thickness of the drive shaft. When bonded to the cutter 52 with a suitable adhesive, the drive shaft 60 and cutter present a generally uniform diameter passageway that opens into a cupped portion of the cutting member 52.

To effect rotation of the cutting member 52, the attending physician grasps the proximally located knob 62 and rotates it. This transmits a torque to the drive shaft 60 which is transmitted the length of the catheter to the cutting member 52. By simultaneously controlling the axial positioning of the cutting member 52 and rotation of the cutting member, the physician can separate material that has been forced into the cavity 50 as the balloon 14 expands.

Between its proximal and distal ends the catheter constitutes a flexible tubular body 70. Techniques for constructing such a catheter body are known in the prior art. One technique is to construct a braided tubular catheter in accordance with the teaching of U.S. Pat. Nos. 3,485,234 and 3,585,707 to Stevens. The subject matter of these patents is incorporated by reference.

The proximal end of the catheter body 70 fits into the bifurcating adaptor 32 and is adhesively bonded to the adaptor 32. Since the inner diameter of the catheter body 70 is greater than the outer diameter of the drive shaft 60, an annular space 72 extends the length of the catheter from the bifurcating adaptor 32 to the catheter's distal end. Fluid pumped into the bifurcating adaptor via the leur fitting 38 enters this passageway 72 and travels the length of the catheter to the region of the balloon 14.

At a distal end, the catheter body 70 engages a cylindrical plastic tube 74 which defines the cavity 50 and the opening 20 through which deposits enter the cavity 50. The balloon 14 is bonded to this tube 74 opposite the side opening 20 along the region of the cavity 50. The tube 74 also defines an opening 76 for routing fluid injected into a proximal end of the catheter into the balloon 14. The balloon 14 is adhesively attached to the tube and includes an opening 78 bounded by a lip that fits into the opening 76 formed in the tube 74.

The catheter 10 includes two annular guides 80, 82 that concentrically position the drive shaft 60 and cutting member 52 at the catheter's proximal and distal ends. An O-ring seal 84 is fixed within a slot of the first guide 80 and allows relative rotation between the cutting member 52 and the catheter 10 without allowing fluid exchange between the two cavities 50, 72.

A flexible elongated core 110 for extracting deposits from the cavity 50 is shown (FIG. 2) extending through the drive shaft 60. The core 110 preferably includes a first tightly coiled metallic wire 112 supporting a second spirally wound metallic wire 114. The inner wire 112 can be coated with a plastic material to form a generally fluid tight coiled cylinder which slips over the guidewire 16. The second, spirally wound wire 114 defines a pumping surface which withdraws or retracts materials separated from the vessel inner wall lining into the center passageway of the drive shaft 60 as the core 110 is rotated.

The core 110 is similar in construction to the structure disclosed in commonly assigned U.S. Pat. No. 4,857,046 to Stevens. The disclosure of this patent is incorporated herein by reference. Unlike the structure disclosed in the '046 Stevens patent, the FIG. 2 core 110 does not include an enlarged distal tip. This allows the distal end of the core 110 to be pushed through the close fitting inner dimensions of the drive shaft 60. Since the guidewire 16 extends completely through the cavity 50 at the catheter's distal tip, the ore member 110 can be guided into and through the cavity 50. A cylindrical well 116 formed within a proximal portion of the tip 14 allows the core 110 to extend completely through the cavity 50 and defines a travel limit for the core 110.

At their proximal ends, the inner 112 and outer 114 wire coils are attached to a cylindrical metal coupling 120 for rotating the elongated member 110. The coupling 120 is attached to an output shaft 122 of a motor (not shown) by a coupling 126 that fits over the shaft 122 and is fixed to the shaft by a threaded connector 128.

A suitable motor for energizing the core 110 is disclosed in issued U.S. Pat. No. 4,917,085 to Smith. The disclosure of this patent is incorporated herein by reference. The motor disclosed in this patent is particularly suited for this application since a throughpassage in the motor's output shaft allows the guidewire 16 to remain in place as the motor's shaft 122 is slipped over the guidewire and the coupling 126 attached to the shaft 122 by means of the connector 128.

OPERATION

In operation, the attending physician monitors positioning of the catheter's distal end as it is routed into the subject. Once the catheter has been properly oriented with regard to diseased or obstructed regions of the vessel, the balloon 18 is inflated and the cutting member 52 manipulated to separate deposits from the inner wall linings of the vessel, typically the blood vessel. With use, the cavity 50 may become completely filled with such deposits and the core 110 inserted into the catheter 10 and routed along the guidewire 16 until the core 110 reaches the cavity 50. When so positioned, rotation of the core 110 with respect to the catheter 10 causes deposits within the cavity 50 to move along the pumping surface of the core 110 into the drive shaft 60. Through suitable coordination of separation motion of the cutting member 52 and actuation of the core 110, the attending physician can maintain a relatively deposit free cavity 50 for receipt of additional deposits. In the event the entire length of the catheter drive shaft 60 becomes filled with such deposits, the attending physician can withdraw the core 110, clean the outer surface of the core, and reinsert it along the guidewire 116 for further vessel treatment.

A preferred embodiment of the invention has been described with a degree of particularity. It is the intent, however, that the invention include all modifications and alterations from the disclosed design falling within the spirit or scope of the appended claims.

I claim

1. Apparatus comprising:
   a) a catheter having an elongated catheter body and a distally located cutting member for separating deposits from inner wall linings of a subject vessel; said catheter including a cavity near its distal end for receipt of deposit is separated from the inner wall lining of said vessel by the cutting member;
   b) a distally located balloon for forcing a distal end of the catheter against the deposits to cause the deposits to enter the cavity through an opening in a sidewall of the catheter for separation by the cutting member; and
   c) elongated means insertable into the catheter body for withdrawing the deposits into the catheter body away from the cavity when the elongated means and the catheter body are relatively rotated.

2. Apparatus comprising:
   a) a catheter having an elongated catheter body and a distally located cutting member for separating deposits from inner wall linings of a subject vessel; said catheter including a cavity near its distal end for receipt of deposits separated from the inner wall lining of said vessel by the cutting member;
   b) a flexible transmission which extends through a lumen in the catheter and is connected to the cutting member for rotating the cutting member with respect to the catheter body; and
   c) elongated means insertable into the catheter body for withdrawing the deposits into the catheter body away from the cavity when the elongated means and the catheter body are relatively rotated.

3. The apparatus of claim 2 wherein the flexible transmission defines an elongated transmission passageway from a proximal to a distal end and wherein the elongated means extends through the transmission passageway and is moveable back and forth within said transmission passageway to allow the elongated means to be inserted into the catheter, pushed through the transmission passageway to enter the cavity, and then withdrawn to remove deposits extracted from the cavity.

4. The apparatus of claim 3 wherein the elongated means comprises an elongated pumping surface that spirals about the elongated means.

5. The apparatus of claim 4 wherein the elongated means comprises a tightly coiled wire which defines a centerthrough passage and further wherein said tightly coiled wire supports a more loosely coiled wire to define the pumping surface.

6. A method for removing deposits from a vessel comprising the steps of:
   routing an elongated catheter into a vessel to bring a cavity defined by a distal end of the catheter into proximity with the deposits;
   expanding a balloon at the catheter's distal end to force the deposits into the cavity;
   separating the deposits from a wall of said vessel by engaging said deposits with a cutting device carried by the catheter; and
   moving separated deposits proximally away from the cavity into a body of the elongated catheter by rotating an elongated core within the cavity.

7. The method of claim 6 wherein the cavity within the catheter is generally cylindrical and wherein the elongated core is positioned along a center axis of the generally cylindrical cavity in the catheter as it is rotated.

8. Apparatus comprising:
   a) a catheter having an elongated catheter body that includes a cavity at its distal end for receipt of deposits separated from the inner wall lining of a subject vessel.
   b) a cutting member moveable with respect to the catheter body for entering the cavity and separating deposits from the vessel; and
   c) an elongated core insertable into the catheter body for moving the deposits away from the cavity into the catheter body as the elongated core is rotated with respect to the catheter body;
   d) said elongated core having an outer pumping surface that carries said deposits away from the cavity as the elongated core is rotated.

9. The apparatus of claim 8 further comprising first means for rotating the elongated core and second means for rotating the cutter.

10. Apparatus comprising:
    a) a catheter having an elongated catheter body and a distally located cutting member for separating deposits form inner wall linings of a subject vessel; said catheter including a cavity near its distal end for receipt of deposits separated from the inner wall lining of said vessel by the cutting member;
    b) a distally located balloon for forcing a distal end of the catheter against the deposits to cause the deposits to enter the cavity through an opening in a sidewall of the catheter for separation by the cutting member; and
    c) elongated means insertable into the catheter body and means proximally coupled to one of the elongated means and the catheter body for inducing relative rotation between the elongated means relative to the catheter body, the elongated means adapted for withdrawing the deposits into the catheter body away from the cavity when the elongated means and the catheter body are relatively rotated.

11. Apparatus comprising:
    a) a catheter having an elongated catheter body and a distally located cutting member for separating deposits from inner wall linings of a subject vessel; said catheter including a cavity at its distal end for receipt of deposits separated from the inner wall lining of said vessel by the cutting member;
    b) a flexible transmission which extends through a lumen in the catheter and is connected to the cutting member for rotating the cutting member with respect to the catheter body;
    c) elongated means insertable into the catheter body for rotating the elongated means relative to the catheter body, the elongated means adapted for withdrawing the deposits into the catheter body away from the cavity as the elongated means and the catheter body are relatively rotated; and
    d) means proximally coupled to the flexible transmission and to one of the elongated means and the catheter body for rotating the cutting member with respect to the catheter body and for inducing relative rotation between the elongated means and the catheter body.

* * * * *